(12) United States Patent
Pochet et al.

(10) Patent No.: US 8,927,520 B2
(45) Date of Patent: Jan. 6, 2015

(54) ANTIBACTERIAL COMPOUNDS

(75) Inventors: Sylvie Pochet, Paris (FR); Gilles Labesse, Montpellier (FR); Muriel Gelin, Montpellier (FR); Liliane Assairi, Paris (FR); Olivier Dussurget, Paris (FR); Guillaume Poncet-Montange, San Francisco, CA (US)

(73) Assignees: Institut Pasteur, Paris (FR); Institut Curie, Paris (FR)

( * ) Notice: Subject to any disclaimer, the term of this patent is extended or adjusted under 35 U.S.C. 154(b) by 30 days.

(21) Appl. No.: 13/976,826

(22) PCT Filed: Dec. 22, 2011

(86) PCT No.: PCT/IB2011/055905
§ 371 (c)(1),
(2), (4) Date: Aug. 26, 2013

(87) PCT Pub. No.: WO2012/090136
PCT Pub. Date: Jul. 5, 2012

(65) Prior Publication Data
US 2013/0331351 A1    Dec. 12, 2013

(30) Foreign Application Priority Data
Dec. 27, 2010 (EP) .................................... 10290679

(51) Int. Cl.
| A01N 43/04 | (2006.01) |
| C07H 19/16 | (2006.01) |
| A61K 31/70 | (2006.01) |
| C07H 19/167 | (2006.01) |
| C12Q 1/48 | (2006.01) |

(52) U.S. Cl.
CPC .............. *C07H 19/16* (2013.01); *C07H 19/167* (2013.01); *C12Q 1/485* (2013.01)
USPC ................ 514/46; 514/43; 514/45; 536/27.1; 536/27.11; 536/27.13; 536/27.2; 536/27.3; 536/27.31

(58) Field of Classification Search
None
See application file for complete search history.

(56) References Cited

PUBLICATIONS

Poncet-Montange, G. et al. "NAD Kinases Use Substrate-assisted Catalysis for Specific Recognition of NAD", The Journal of Biological Chemistry, vol. 282, No. 47, pp. 33925-33934, (Aug. 2007), (XP002626205).
Gunji H. et al. "Oligonucleosides with a Nucleobase-Including Backbone, Part 3, Synthesis of Acetyleno-Linked Adenosine Dimers", Helvetica Chimica Acta, vol. 83, No. 11, pp. 2975-2992, (Nov. 2000), (XP55024809).
Written Opinion of the International Search Authority Issued in PCT/IB11/055905 Filed Dec. 22, 2011.
International Search Report Issued Apr. 25, 2012 in PCT/IB11/055905 filed Dec. 22, 2011.

*Primary Examiner* — Patrick Lewis
(74) *Attorney, Agent, or Firm* — Oblon, Spivak, McClelland, Maier & Neustadt, L.L.P.

(57) ABSTRACT

The present invention relates to compounds of formula (I): wherein Rj, R2, R3, R4, Xi, X2, X3 and Z are as defined in claim 1. The compounds are useful in the prevention and/or treatment of bacterial infections.

(I)

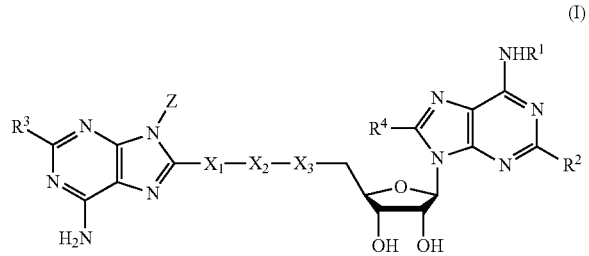

18 Claims, 3 Drawing Sheets

ANTIBACTERIAL COMPOUNDS

The present invention relates to compounds for use in the prevention and/or treatment of bacterial infections, pharmaceutical compositions comprising them, and processes for the preparation thereof.

The search for new antibacterial compounds has become increasingly important with the emergence of antibiotic resistance worldwide (1).

In this regard, NAD kinases (NADKs, EC 2.7.1.23) represent an attractive and novel drug target for antibiotic discovery. NADKs are ubiquitous enzymes involved in the last step of the biosynthesis of NADP catalyzing the transfer of a phosphate group on the substrate NAD to produce NADP in the presence of both ATP and $Mg^{2+}$ NADKs are also involved in the tight regulation of the NADH/NADPH ratio (8). Both NAD(P) and NAD(P)H are essential cofactors for a large number of enzymes involved in various metabolic pathways such as oxidoreductases. It is therefore not surprising that NADKs were recently shown to be essential for growth in many bacteria (2-4) including various human pathogens such as *Mycobacterium tuberculosis* (5), *Staphylococcus aureus* (6), *Streptococcus pneumoniae* (7), *Salmonella enterica* (8), and *Pseudomonas aeruginosa*. Besides, while the activity of NADKs has been well known for decades, their genes were cloned only recently (9), subsequently leading to rapid identification of NADK orthologs in many organisms from bacteria, Archaea, plants, and human (Pfam PF01513). Advantageously, it has been shown that bacterial and human enzymes show significant functional and sequence divergences, and the NADK activity in human cells is low (10). Inhibitors of NADKs should therefore prove to be useful as antibiotics, thereby warranting the search for such inhibitors.

Di-5'-thioadenosine (DTA) has thus been recently reported to be a synthetic inhibitor of the NADK from *Listeria monocytogenes* (11). This compound inhibits NADK with a micromolar affinity (K≈0.02 mM). However, its antibacterial activity, and hence its potential efficiency as an antibiotic have not been assessed.

Accordingly, it is an object of the present invention to provide alternative compounds useful for treating bacterial infections.

The present invention is thus directed, in one aspect, to various compounds of structure:

(A)

and its tautomeric, stereoisomeric forms, mixtures of stereoisomeric forms, or pharmaceutically acceptable salt forms thereof, wherein the constituent members are defined infra.

Another object of the present invention is to provide pharmaceutical compositions comprising the compounds of the present invention wherein the compositions comprise one or more pharmaceutically acceptable excipients and a therapeutically effective amount of at least one of the compounds of the present invention, or a pharmaceutically acceptable salt thereof.

Another object of the present invention is to provide compounds of formula (A) or (I) for use in the prevention and/or treatment of bacterial infections.

Another object of the present invention is to provide methods of treating or preventing bacterial infections comprising the administration of a therapeutically effective amount of a compound of formula (A) or (I) to a patient in need thereof.

These and other objects, features and advantages of the compounds of formula (A) or (I) will be disclosed in the following detailed description of the patent disclosure.

Compounds of Formula (A) and (I)

In a first object, the present invention provides compounds of formula (A):

(A)

Wherein $R_1$ is H, $C_1$-$C_6$ alkyl, $C_2$-$C_6$ alkenyl, or $C_2$-$C_6$ alkynyl, said alkyl, alkenyl or alkynyl being optionally substituted by $SR_5$, $NR_5R_{5A}$ or $OR_5$;

$R_2$ is H, F, Cl, Br, I, $OR_6$, or $NHR_7$;

$R_3$ is H, Cl, Br, F, I, $OR_8$, or $NHR_9$;

$R_4$ is H, Cl, Br, F, I, $CH_3$, $SCH_2COOH$, $SR_{10}$, $SeR_{11}$, $CH_2R_{12}$, $C\equiv CR_{13}$, $CH=CHR_{14}$ or $S(CH_2)_nC(=O)R_{17}$;

$X_1$ is —S—, —Se—, —$CH_2$—, —CH=CH—, or —C≡C—;

$X_2$ is a single bond, $C_1$-$C_4$ alkylene, $C_2$-$C_4$ alkenylene, or $C_2$-$C_4$ alkynylene;

$X_3$ is —NHC(=O)—, —C(=O)NH—, —$NR_{15}$—, —$SO_2NH$—, —$NHSO_2$—, —$CH_2$—, —O—, —S—;

Z is selected from

Or

Z is $C_6$-$C_{10}$ aryl, 5 to 7 membered heteroaryl, arylalkyl or heteroarylakyl, wherein said aryl and heteroaryl are optionally substituted with 1 to 3 $R_0$ groups;

$R_0$ is F, Cl, Br, I, OH, $NH_2$, $NO_2$, $C_1$-$C_6$ alkyl, $C_2$-$C_6$ alkenyl, or $C_2$-$C_6$ alkynyl;

$R_5$, $R_{5A}$, $R_6$, $R_7$, $R_8$, $R_9$, $R_{15}$ are each independently selected from H, $C_1$-$C_6$ alkyl, $C_2$-$C_6$ alkenyl, or $C_2$-$C_6$ alkynyl;

$R_{10}$, $R_{11}$, $R_{12}$, $R_{13}$ and $R_{14}$ are each independently selected from $C_1$-$C_6$ alkyl, $C_2$-$C_6$ alkenyl, or $C_2$-$C_6$ alkynyl;

$R_{16}$ is OH, $NH_2$, $N_3$ or $OCH_2CH=CH$;

$R_{17}$ is OH or $NH(CH_2)_pAr$, wherein Ar is an aryl group optionally substituted by Br, C≡CH;

m is 0 or 1;

n is 1, 2 or 3;

p is 1, 2 or 3;

and the tautomeric, stereoisomeric forms, mixtures of stereoisomeric forms or pharmaceutically acceptable salt forms thereof.

In another aspect, the present invention provides compounds of formula (I):

(I)

Wherein $R_1$ is H, $C_1$-$C_6$ alkyl, $C_2$-$C_6$ alkenyl, or $C_2$-$C_6$ alkynyl, said alkyl, alkenyl or alkynyl being optionally substituted by $SR_5$, $NR_5R_{5A}$ or $OR_5$;

$R_2$ is H, F, Cl, Br, I, $OR_6$, or $NHR_7$;

$R_3$ is H, Cl, Br, F, I, $OR_8$, or $NHR_9$;

$R_4$ is H, Cl, Br, F, I, $CH_3$, $SCH_2COOH$, $SR_{10}$, $SeR_{11}$, $CH_2R_{12}$, $C{\equiv}CR_{13}$, or $CH{=}CHR_{14}$;

$X_1$ is —S—, —Se—, —$CH_2$—, —CH=CH—, or —C≡C—;

$X_2$ is $C_1$-$C_4$ alkylene, $C_2$-$C_4$ alkenylene, or $C_2$-$C_4$ alkynylene;

$X_3$ is —NHC(=O)—, —C(=O)NH—, —$NR_{15}$—, —$SO_2NH$—, —$NHSO_2$—, —$CH_2$—, —O—, —S—;

Z is or Z is $C_6$-$C_{10}$ aryl or 5 to 7 membered heteroaryl, wherein said aryl and heteroaryl are optionally substituted with 1 to 3 $R_0$ groups;

$R_0$ is F, Cl, Br, I, OH, $NH_2$, $NO_2$, $C_1$-$C_6$ alkyl, $C_2$-$C_6$ alkenyl, or $C_2$-$C_6$ alkynyl;

$R_5$, $R_{5A}$, $R_6$, $R_7$, $R_8$, $R_9$, $R_{15}$ are each independently selected from H, $C_1$-$C_6$ alkyl, $C_2$-$C_6$ alkenyl, or $C_2$-$C_6$ alkynyl;

$R_{10}$, $R_{11}$, $R_{12}$, $R_{13}$ and $R_{14}$ are each independently selected from H, $C_1$-$C_6$ alkyl, $C_2$-$C_6$ alkenyl, or $C_2$-$C_6$ alkynyl;

$R_{16}$ is H, F, Cl, Br, I, OH, $NH_2$, $N_3$ or $OCH_2C{\equiv}CH$;

and the tautomeric, stereoisomeric forms, mixtures of stereoisomeric forms or pharmaceutically acceptable salt forms thereof.

In certain aspects, there are included compounds of formula (A) or (I), wherein —$X_1$—$X_2$—$X_3$— is selected from —S—$CH_2$—C(=O)NH—, —C≡C—$CH_2$—NH—, —C≡C—$CH_2$—O—, —C≡C—C(=O)NH—, or —C≡C—$CH_2$—NH—C(=O)—.

In certain aspects, there are included compounds of formula (Ia):

(Ia)

Wherein $R_1$, $R_2$, $R_3$, $R_4$, $X_2$, $X_3$ and Z are as defined above.

In another aspect, there are included compounds of formula (Ia) wherein $X_3$ is —O— or —NH—.

In yet another aspect, there are included compounds of formula (Ib):

(Ib)

Wherein $R_1$, $R_2$, $R_3$, $R_4$, $X_2$, and Z are as defined above.

In a preferred aspect, there are included compound of formula (A) or (I) wherein $X_2$ is $C_1$-$C_4$ alkylene, more preferably —$CH_2$—.

In other aspects of the present invention, there are included compounds of formula (A) or (I) wherein Z is In other aspects of the present invention, there are included compounds of formula (A) or (I) wherein $R_{16}$ is OH or $NH_2$, notably $NH_2$.

In additional aspects of the present invention, there are included compounds of formula (A) or (I) wherein $R_1$ is H.

In certain aspects, there are included compounds of formula (A) or (I) wherein $R_3$ is H.

In other aspects of the present invention, there are included compounds of formula (A) or (I) wherein $R_2$ is H.

In other aspects of the present invention, there are included compounds of formula (A) or (I) wherein $R_4$ is H.

Preferably, the compound of formula (A) or (I) for use in the prevention or treatment of bacterial infections is selected from:

5'-amino-5'-deoxyadenosin-8-yl-thio-N-[(5'-amino-5'-deoxyadenosine)methyl]acetamide;

8-[3-N-(5'-deoxyadenosyl)aminoprop-1-ynyl]adenosine;

8-[3-(5'-deoxyadenosyl)methoxyprop-1-ynyl]adenosine.

Pharmaceutical Compositions

In another object, the present invention relates to a pharmaceutical composition comprising a compound of formula (A) or (I) as defined above, in admixture with one or more pharmaceutically acceptable excipients.

Compounds of Formula (A) or (I) for Use in the Treatment and/or Prevention of Bacterial Infections In another object, the present invention relates to a compound of formula (A) or (I) for use in the prevention and/or treatment of bacterial infections, notably Gram positive infections, in particular Gram positive coccus infections Method of Preparation of Compounds of Formula (A) or (I)

The compounds of the present invention may be prepared in a number of methods well known to those skilled in the art, including, but not limited to those described below, or through modifications of these methods by applying standard techniques known to those skilled in the art of organic synthesis. The reagents and starting materials are commercially available, or readily synthesized by well-known techniques by one of ordinary skill in the arts. All substituents, unless otherwise indicated, are as previously defined. All processes disclosed in association with the present invention are contemplated to be practiced on any scale, including milligram, gram, multigram, or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from active starting materials or by deliberate chiral synthesis of target centers.

As will be readily understood, functional groups present on the compounds of Formula I may contain protecting groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Other preferred protecting groups according to the invention may be found in Greene, T. W. and Wuts, P.G.M., "Protective Groups in Organic Synthesis" 2d. Ed., Wiley & Sons, 1991, or in P. J. Kocienski, "Protecting Groups", 3d. Ed., Thieme, Stuttgart, N.Y., 2004.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography, in particular High Performance Liquid Chromatography (HPLC).

In another object, the present invention relates to a method for preparing a compound of formula (Ia) as defined above, said method comprising the steps of:

i. Coupling a compound of formula (IIa) with a compound of formula (IIIa), (IIa)

(IIIa)

Wherein
$R_1$, $R_2$, $R_3$, $R_4$, $X_2$, $X_3$ and Z are as defined above,
Hal is Br, I, or Cl,
the hydroxyl groups, when present, being protected by a hydroxyl protecting group (Pr), ii. Deprotecting the hydroxyl groups of the obtained compound, and optionally iii. Recovering the obtained compound of formula (Ia).

In a preferred aspect, step i) is a Sonogashira coupling which method is well known to those skilled in the art. In particular, this coupling may be carried out in the presence of triethylamine (TEA), CuI and Pd(PPh$_3$)$_4$ in a polar aprotic solvent such as THF.

The hydroxyl groups can be protected by acetyl groups (Ac). After coupling according to step i), these protecting groups can be removed, for example by contacting the obtained product with aqueous ammonia in methanol, at 50° C.

In still further aspects, the compound of formula (IIIa) can be obtained from the corresponding compound of formula (IVa):

(IVa)

Wherein $R_1$, $R_2$, $R_4$, and $X_3$ are as defined above,

Generally, the reaction of conversion of (IVa) into (IIIa) is performed in the presence of HC≡C—$X_2$—Br, such as propargyl bromide, a base, in a polar aprotic solvent.

In another object, the invention relates to a method for preparing a compound of formula (Ib) as defined above, said method comprising the steps of:

i. Coupling a compound of formula (IIb) with a compound of formula (IIIb), (IIb)

(IIIb)

Wherein
$R_{17}$ is $OR_{18}$, or Hal,
Hal is Br, Cl, or I, preferably Cl,
$R_{18}$ is H, $C_1$-$C_6$ alkyl, or is such that $C(=O)OR_{18}$ forms an activated ester;
Z is as defined above, the hydroxyl groups, when present, being protected by an hydroxyl protecting group;

i. Deprotecting the hydroxyl groups of the obtained product; and optionally
ii. Recovering the obtained compound of formula (Ib).

As used herein, "activated ester" means an ester which can easily undergo a peptide coupling with the amine of formula (IIIb). Thus, to enhance the electrophilicity of the corresponding carboxylate group, the negatively charged oxygen is first "activated" into a better leaving group. Such activated esters can be obtained according to methods well known from those skilled in the art, notably by reacting the carboxylate compound with an activating agent. As examples of activating agents, mention may be made notably of carbodiimides, such as dicyclohexylcarbodiimide (DCC), 1-ethyl-3-(3-dimethylaminopropyl)carbodiimide hydrochloride (EDC. HCl), or triazoles, such as 1-hydroxy-benzotriazole (HOBt) or 1-hydroxy-7-aza-benzotriazole (HOAt).

According to a further aspect, the compound of formula (IIb) can be obtained from the corresponding compound of formula (IVb):

(IVb)

Wherein $R_3$ and Z are as defined above, and Hal is Cl, Br or I.

Generally, the reaction is carried out in the presence of thioglycolic acid, NaH, in a polar aprotic solvent such as DMF, at room temperature, ie between 20-25° C.

In still further aspects of the present invention, the compound of formula (IVb) can be obtained from the corresponding compound of formula (Vb):

(Vb)

Wherein, $R_3$ and Z are as defined above.

Generally the reaction of converting the compound (Vb) into (IVb) is carried out in the presence of NBS in a polar aprotic solvent, such as DMF.

The above reactions can be carried out by the skilled person by applying or adapting the methods illustrated in the examples hereinafter.

Chemical Probes and Screening Method

In another object, the invention also relates to a chemical probe comprising a compound of formula (A) or (I) as defined above, coupled to a detectable label.

Preferably, the compound of formula (A) or (I) is a compound wherein $R_{16}$ is $NH_2$ Or $N_3$.

A wide variety of detectable labels may be used, such as those disclosed notably in "The Molecular Probes® Handbook", 11th Edition Thus, the compound of formula (I) may be coupled to a fluorescent molecule, such as fluorescein or rhodamin, either directly or indirectly via a homo- or heterobifunctional linker such as biotine.

The detectable label is preferably coupled to the compound of formula (I) via a covalent bond, either directly or indirectly via a homo- or heterobifunctional agent, for example via glutaraldehyde. This covalent bond may be notably a —NH—C(=O)— bond.

In another object, the invention also relates to a method for screening molecules inhibiting NAD kinase, said method comprising the steps of:

i. contacting NAD kinase with a chemical probe as defined above with a molecule to be screened;
ii. determining the quantity of chemical probe bound or unbound to said NAD kinase; and
iii. deducing therefrom if the screened molecule is an inhibitor of the said NAD kinase.

Definitions

The following terms and expressions contained herein are defined as follows:

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$-$C_6$ alkyl" refers to an alkyl radical containing from 1 to 6 carbon atoms.

As used herein, the term "alkenyl" refers to a straight chain, or branched hydrocarbon chains of 2 to 6 carbon atoms having at least one carbon-carbon double bond.

A designation "$C_2$-$C_6$ alkenyl" refers to an alkenyl radical containing from 2 to 6 carbon atoms. Examples of alkenyl groups include ethenyl, propenyl, isopropenyl, 2,4-pentadienyl. "$C_2$-$C_4$ alkenyl" are particularly preferred.

As used herein, the term "alkynyl" refers to a straight chain, or branched hydrocarbon chains of 2 to 6 carbon atoms having at least one carbon-carbon triple bond. A designation "$C_2$-$C_6$ alkynyl" refers to an alkynyl radical containing from 2 to 6 carbon atoms. Examples include ethynyl, propynyl, isopropynyl. "$C_2$-$C_4$ alkynyl" are particularly preferred.

As used herein, the term "alkylene" refers to a substituted or unsubstituted, branched or straight chained hydrocarbon of 1 to 4 carbon atoms, which is formed by the removal of two hydrogen atoms. A designation such as "$C_1$-$C_4$ alkylene" refers to an alkylene radical containing from 1 to 4 carbon atoms. Examples include methylene (—$CH_2$—), propylidene ($CH_3CH_2CH$=), 1,2-ethandiyl (—$CH_2CH_2$—), etc.

As used herein, "alkenylene" refers to a divalent group derived from a straight or branched chain hydrocarbon containing at least one carbon-carbon double bond. Examples of alkenylene include —CH=CH—, —$CH_2$CH=CH—, —C($CH_3$)=CH—, —$CH_2$ CH=$CHCH_2$—, and the like.

As used herein, "alkynylene" refers to a divalent group derived by the removal of two hydrogen atoms from a straight or branched chain acyclic hydrocarbon group containing a carbon-carbon triple bond.

As used herein, the term "aryl" refers to a substituted or unsubstituted, mono- or bicyclic hydrocarbon aromatic ring system having 6 to 10 ring carbon atoms. Examples include phenyl and naphthyl.

As used herein, the term "heteroaryl" refers to an aromatic group containing 5 to 10 ring carbon atoms, preferably 5 to 7, in which one or more ring carbon atoms are replaced by at least one hetero atom such as —O—, —N—, or —S—. Examples of heteroaryl groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, the term "arylalkyl" refers to an alkyl group that is substituted with an aryl group wherein, said aryl and alkyl groups are as defined above.

Preferably, the alkyl is a lower alkyl group. Examples of arylalkyl groups include, but are not limited to benzyl, phenethyl or naphthylmethyl.

As used herein, the term "heteroarylalkyl" refers to an alkyl group that is substituted with an heteroaryl group wherein, said aryl and alkyl groups are as defined above. Preferably, the alkyl is a lower alkyl group.

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

The meanings of all the other terms used in the description of the present invention are well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically acceptable salts, other salts are included in the invention. They may serve as intermediates in the purification of the compounds, in the preparation of other salts, or in the identification and characterization of the compounds or intermediates.

Other features of the invention will become apparent in the course of the following descriptions of exemplary embodiments. These examples are given for illustration of the invention and are not intended to be limiting thereof.

FIGURES

100 µL suspensions of *S. aureus* corresponding to $2.10^3$ bacteria were incubated overnight at 37° C. with increasing concentrations of inhibitor (1 to 100 µg/mL). Bacterial killing (percent) was determined as the ratio of colony forming units after incubation with inhibitor to that of colony forming units after incubation with buffer alone. Data are mean values ±SD from three separate experiments. * indicates a statistical significance in Student's t-test of p<0.05.

EXAMPLES

I. Chemical Synthesis

A. General

Reagents and solvents for synthesis were obtained from commercial suppliers and used without further purification. Standard nucleosides and nucleotides were obtained from commercial suppliers. 5'-Methylthio-5'-deoxyadenosine (MTA, 1) was commercially available. Flash chromatography was performed using silica gel 60 (Merck) and the indicated solvent mixtures. Preparative and analytical HPLC were carried out on an Agilent system (1100 series) using a C18 reverse phase column (Kromasil, 5μ 100 Å) at a flow rate of 4.0 ml/min or 1 ml/min and a linear gradient of $CH_3CN$ in 20 mM triethylammonium acetate buffer (TEAA) at pH 7.0 over 20 min. $^1H$ and $^{13}C$ NMR spectra were recorded on a Bruker Avance 400 spectrometer, operating at 400.13 MHz and 100.62 MHz, respectively. Chemical shifts are given in ppm (δ), coupling constants (J) are reported in Hertz and the normal abbreviations are used. High resolution mass spectra were recorded on a Waters Q-TOF micro MS instrument using a mobile phase of acetonitrile/water with 0.1% formic acid.

B. Synthesis of Monomeric Blocks

5'-Bromo-5'-deoxyadenosine (2) was synthesized by direct halogenation of adenosine [12]. 5'-Fluoro-5'-deoxyadenosine (3) [1,3] and 5'-azido-5'-deoxyadenosine (6) were prepared starting from 2',3'-O-isopopylidene-adenosine. 5'-Amino-5'-deoxyadenosine (7) was obtained by catalytic hydrogenation of 5'-azido-5'-deoxyadenosine (6). 8-Bromo nucleosides 8 and 9 were obtained by reacting 6 and 7 with NBS in anhydrous DMF. 5'-O-Propargylic derivative 4 was obtained by reacting propargyl bromide in the presence of NaH with $N^6$-benzoyl-2',3'-O-isopopylidene-adenosine according to reported procedure [1,4], followed by removal of protecting groups.

5'-N-Propargylamino-5'-deoxyadenosine (5)

5

1) NH$_2$NH$_2$·H$_2$O, abs. EtOH, 80° C., 90 min; 2) propargyl bromide, DIEA, DMF, 0° C., 18 h; 3) 80% formic acid, 30° C., overnight.

The synthesis of compound 5 is outlined in Scheme 1. Amino 12 was synthesized in two steps from 2′,3′-O-isopropylidene-adenosine via the phthalimido-adenylate 11 according to Kolb and co-workers [1,5]. To a solution of 12 (0.31 g, 0.8 mmol) in anhydrous DMF (8 mL) was added propargyl bromide (80% in toluene) (1.1 eq.) and DIEA (4 eq.) at 0° C. After stirring overnight at 4° C., the reaction mixture was evaporated to dryness and purified by flash chromatography (CH$_2$Cl$_2$/MeOH, 9/1) gave 13 (0.18 g, 65%). Treatment of 13 (90 mg, 0.26 mmol) with 80% formic acid in water (3 mL) at 30° C. overnight gave 5 (68 mg, 85%) after purification by flash chromatography (CH$_2$Cl$_2$/MeOHNH$_4$OH, 90/10/1). $^1$H NMR (MeOD) δ 2.73 (t, 1H, CH), 3.10 (d, 2H, H5′ and H5′), 3.53 (t, 2H, NCH$_2$), 4.24 (m, 1H, H4′), 4.34 (t, 1H, H3′), 4.87 (t, 1H, H2′), 5.98 (d, 1H, H1′, J=4.4 Hz), 8.25 (s, 1H, H2), 8.29 (s, 1H, H8); $^{13}$C NMR (MeOD) δ 37.17 (NCH$_2$), 49.85 (C5′), 71.95 (C3′), 72.60 (CH), 73.20 (C2′), 79.90 (Cq), 83.48 (C4′), 89.51 (C1′), 119.48 (C5), 140.63 (C8), 149.06 (C4), 152.44 (C2), 155.96 (C6); HRMS (ESI-TOF) m/z calcd for C$_{13}$H$_{16}$N$_6$O$_3$ (M+H) 305.1362; found 305.1348.

8-Carboxymethylthio-5′-azido-5′-deoxyadenosine (10)

A solution of thioglycolic acid (0.2 mmol) and NaH (0.4 mmol, 60% in oil) in anhydrous DMF (2 mL) was stirred for 10 min, then 8-bromo-5′-azido-5′-deoxyadenosine (8) (50 mg, 0.13 mmol) in DMF (1 mL) was added at 0° C. After 8 h at room temperature, more thioglycolate (0.2 mmol) in DMF was added. After stirring overnight, the reaction mixture was concentrated to dryness and the residue purified by reverse phase HPLC (10-30% ACN in TEAA over 20 min) to give 10 (28 mg, 56%); UV λmax 279 nm; HRMS (ESI-TOF) m/z calcd for C$_{12}$H$_{14}$N$_8$O$_5$S (M+H) 383.0886; found 383.0890.

C. Synthesis of ligands 17, 19 and 21

5′-Amino-5′-deoxyadenosin-8-yl-thio-N-[(5′-amino-5′-deoxy-adenosine)methyl]acetamide (17)

Scheme 2:

-continued

17

1) NBS, DMF, rt, 2 days; 2) thioglycolic acid, NaH, DMF, rt, 18 h; 3) 12, PyBOP, DIEA, DMF, rt, 18 h; 4) NH$_2$NH$_2$·H$_2$O, 80° C., 90 min; then 80% formic acid, 30° C., 5 h.

The synthesis of bi-ligand 17 is outlined in Scheme 2. Reaction of phthalimidoadenylate 11[4] with NBS (2 eq.) in anhydrous DMF at room temperature for 2 days afforded 14 in 40% yield after purification by flash chromatography (CH$_2$Cl$_2$/MeOH, 95/5). To a stirred solution of thioglycolic acid (2 mmol) and NaH (60% in oil, 4 mmol) in anhydrous DMF (10 mL) was added compound 14 (0.51 g, 1 mmol) in DMF (1 mL). After stirring overnight at room temperature, the reaction mixture was concentrated to dryness. The residue was taken up in water and extracted with AcOEt (3 times). The organic layers were dried, concentrated and purified by flash chromatography (CH$_2$Cl$_2$/MeOH) to give 15 (0.27 g, 51%). To compound 15 (29 mg) and 5'-amino-2',3'-O-isopropylidene-adenosine (12) (22 mg, 1.3 eq.) in anhydrous DMF (2 mL) were added PyPOB (29 mg, 1 eq.) and DIEA (3 eq.). After stirring overnight at room temperature, the reaction mixture was concentrated to dryness. The residue was purified by flash chromatography (CH$_2$Cl$_2$/MeOH, 95/5) to give 16 (38 mg, 85%). Compound 16 (34 mg) was treated with hydrazine hydrate (0.02 mL, 16 eq.) in abs, ethanol (2 mL). After 90 min at 80° C., the reaction was complete and the solvent was removed by evaporation. The residue was taken up in water, acetic acid was added until pH 4, then the reaction mixture was lyophilized. The crude product (30 mg) was treated with 80% aq. formic acid (1.5 mL) at 30° C. for 5 h. The reaction mixture was neutralized by addition of aq. ammonia and then lyophilized. Purification by reverse phase HPLC (5-40% ACN in TEAA over 20 min) gave compound 17 (10 mg, 38% two steps). Rt (5 to 40% ACN in TEAA in 20 min) 5.1 min; $^1$H NMR (DMSO-d$_6$) δ: 2.82 (m, 2H, H5'a and H5''a), 3.47 (m, 2H, H5'b and H5''b), 3.88 (m, 1H, H4'a), 4.01 (m, 1H, H4'b), 4.12 (m, 3H, H3'b and CH$_2$), 4.21 (dd, 2H, H3'a), 4.71 (t, 1H, H2'b), 5.04 (t, 1H, H2'a), 5.77 (d, 1H, H1'a, J=6.2 Hz), 5.87 (d, 1H, H1'b, J=6.0 Hz), 7.07 (bs, 2H, NH$_2$), 7.28 (bs, 2H, NH$_2$), 8.08 (s, 1H, H2), 8.28 (s, 1H, H2), 8.33 (s, 1H, H8), 8.63 (bs, 1H, NH); $^{13}$C NMR (DMSO-d$_6$) δ: 36.61 (CH$_2$), 41.97 (C5'a), 44.11 (C5'b), 70.75 (CH$_2$), 71.26 (C3'b), 71.47 (C2'b), 71.70 (C3'a), 73.15 (C2'a), 83.77 (C4'a), 86.48 (C4'b), 88.64 (C1'a), 89.05 (C1'b), 119.71 and 119.99 (C5), 140.87 (CH$_8$), 148.81, 149.65 and 151.69 (C8, C4), 152.17 and 153.15 (C2), 154.73 and 156.63 (C6), 167.47 (CO); UV λmax 287 nm; HRMS (ESI-TOF) m/z calcd for C$_{22}$H$_{29}$N$_{12}$O$_7$S (M+H) 604.2030; found 604.2012.

Scheme 3:

11

12

13

18

-continued

19

1) NH₂NH₂•H₂O, abs. EtOH, 80° C., 90 min;
2) propargyl bromide, DIEA, DMF, 4° C., 18 h;
3) 8-bromo-2',3',5'-tri-O-acetyl-adenosine, CuI, Pd(PPh₃)₄, THF, 60° C.;
4) aq. 36% NH₄OH, MeOH, 50° C., 3 h;
5) 80% formic acid, 30° C., 7 h.

8-[3-N-(5'-Deoxyadenosin-5'-yl)aminoprop-1-yn-1-yl]adenosine (19)

Treatment of commercial 8-bromo-adenosine with acetic anhydride (4 eq.) in pyridine gave after purification by flash chromatography (CH₂Cl₂/MeOH) 8-bromo-2',3',5'-tri-O-acetyl-adenosine in 62% yield. To a degassed (3 times) solution of the bromo derivative (0.21 g, 0.45 mmol), alkyne 13 (0.20 g, 0.58 mmol) and triethylamine (3 eq.) in THF (10 mL) was added CuI (10% mol) and Pd(PPh₃)₄ (5% mol). After stirring under Ar at 60° C. overnight, the solvent was evaporated under reduced pressure. The residue was purified by flash chromatography (CH₂Cl₂/MeOH) to give the coupling product 18 (0.17 g, 52%). A solution of 18 (0.13 g, 0.18 mmol) in MeOH (4 mL) and 36% aq. ammonia (2 mL) was heated at 50° C. After 3 h the reaction was complete and the solvent was evaporated under reduced pressure. Purification by flash chromatography (CH₂Cl₂/MeOH) afforded deacetylated product (58 mg, 51% yield). This compound (48 mg) was treated with 80% aq. formic acid (1 mL) at 30° C. After 7 h, the reaction was complete and the reaction mixture was neutralized by addition of aq. ammonia before lyophilisation. The crude product was purified by reverse phase HPLC to give 19 (6 mg, 16%) as a white powder. Rt (5-25% ACN in 20 mM TEAA buffer) 12.3 min; $^1$H NMR (DMSO-d₆) δ: 2.88 (m, 1H, H5'a), 3.01 (m, 1H, H5'a), 3.53 (m, 1H, H5'b), 3.70 (m, 1H, H5'b), 3.76 (d, 2H, NCH₂), 3.98 (m, 1H, H4'b), 4.06 (m, 1H, H4'a), 4.17 (m, 1H, H3'a), 4.21 (m, 1H, H3'b), 4.72 (m, 1H, H2'a), 4.99 (m, 1H, H2'b), 5.18 (bs, 2H, OH), 5.40 (bs, 2H, OH), 5.50 (bs, 1H, OH), 5.86 (d, 1H, H1'a, J=6.1 Hz), 5.96 (d, 1H, H1'b, J=6.7 Hz), 7.24 (bs, 2H, NH₂), 7.57 (bs, 2H, NH₂), 8.15 (s, 1H, H2), 8.17 (s, 1H, H2), 8.35 (s, 1H, H8); UV λmax 262 nm, 279 nm; $^1$HRMS (ESI-TOF) m/z calcd for C₂₃H₂₈N₁₁O₇ (M+H) 570.2173; found 570.2174.

Scheme 4:

1) propargyl bromide, NaH, THF, 4° C., 18 h; 2) 8-bromo-2',3',5'-tri-O-acetyl-adenosine, CuI, Pd(PPh₃)₄, THF, 60° C.; 3) aq. 36% NH₄OH, MeOH, rt, 18 h; 4) 80% formic acid, 30° C., 2 h.

8-[3-(Adenosin-5'-yl)methoxyprop-1-yn-1-yl]adenosine (22)

To a degassed (3 times) solution of 8-bromo-2',3',5'-tri-O-acetyl-adenosine (0.14 g, 0.30 mmol), alkyne 20 [3](0.20 g, 0.44 mmol)) and triethylamine (3 eq.) in THF (10 mL) was added CuI (10% mol) and Pd(PPh$_3$)$_4$ (5% mol). After stirring under Ar at 60° C. overnight, the solvent was evaporated under reduced pressure. The residue was purified by flash chromatography (CH$_2$Cl$_2$/MeOH) to give 21 (0.15 g, 61%) and the dialkyne compound as a secondary product (25%). Compound 21 (54 mg) was reacted with 36% aq. ammonia (2 mL) in methanol (2 mL) at room temperature overnight. After evaporation of the solvent, the crude product was treated with 80% aq. formic acid (1.5 ml) at 30° C. After 2 h the reaction was complete, the reaction mixture was neutalized by addition of diluted acetic acid, then lyophilized. Purification by reverse phase HPLC (13% isocratic) of the crude product gave biligand 22 in 46%. Rt (5 to 40% A in TEAA in 20 min) 13.0 min. $^1$H NMR (DMSO-d$_6$) δ: 3.54 (m, 1H, H5'a), 3.67 (m, 1H, H5''a), 3.77 (m, 1H, H5'b), 3.85 (m, 1H, H5''b), 4.00 (m, 1H, H4'a), 4.10 (m, 1H, H4'b), 4.21 (m, 2H, H3'a and H3'b), 4.60 (m, 2H, CCH$_2$), 4.62 (m, 1H, H2'a), 5.00 (m, 1H, H2'b), 5.50 (bs, 5H, OH), 5.92 (d, 1H, H1'a, J=5.3 Hz), 5.95 (d, 1H, H1'b, J=6.7 Hz), 7.23 (bs, 4H, NH$_2$), 7.63 (bs, 2H, NH$_2$), 8.17 and 8.16 (each s, 2H, 2H2), 8.32 (s, 1H, H8); $^{13}$C NMR (DMSO-d$_6$) δ: 58.75 (C5'a), 62.65 (C5'b), 70.75 (CH$_2$), 71.03 and 71.44 (C4'a, C4'b), 72.15 (C2'a), 73.71 (C2'b), 83.30 (C4'a), 87.18 (C4'b), 87.94 (C1'b), 89.94 (C1'a), 119.50 and 119.84 (C5), 133.43 (C8), 139.83 (CH8), 148.90 and 149.96 (C4), 153.19 and 153.90 (C2), 154.73 and 156.64 (C6); UV λmax 265 nm, 279 nm; HRMS (ESI-TOF) m/z calcd for C$_{23}$H$_{27}$N$_{10}$O$_8$ (M+H) 571.2013; found 571.1993.

Scheme 5

23 R = Br
24 R = SCH$_2$COOH

25

26

8-Bromo-N$^9$-benzyladenine (23)

To a stirred solution of N-benzyladenine [Lambertucci, et al. *Bioorganic and Medicinal Chemistry*, 2009, 17, p 2812-2822](0.22 g, 1.0 mmol) in DMF (10 mL) was added NHS (0.53 g, 3.0 mmol) at room temperature. After stirring overnight, the solvent was evaporated, the residue was purified by flash chromatography (eluted with 1 to 3% MeOH in CH$_2$Cl$_2$) to give 23 (0.15 g, 50%). $^1$H NMR (DMSO-d$_6$) δ 5.36 (s, 2H, CH$_2$), 7.24 (m, 2H, H arom.), 7.30 (m, 1H, H arom.), 7.35 (m, 2H, H arom.), 7.41 (bs, 2H, NH$_2$), 8.17 (s, 1H, H2); $^{13}$C NMR (DMSO-d$_6$) δ: 47.07 (CH$_2$), 119.47 (C5), 126.91 (C8), 127.58, 128.26 and 129.21 (CH), 136.43 (Cq), 151.44 (C4), 153.56 (C2), 155.29 (C6); HRMS (ESI-TOF) m/z calcd for [C$_{12}$H$_{10}$N$_5$Br+H]304.0198 and 306.0178; found 304.0184 and 306.0167.

8-Carboxymethylthio-N$^9$-benzyladenine (24)

A solution of thioglycolic acid (0.05 mL, 0.68 mmol) and NaH (0.05 g, 1.35 mmol, 60% in oil) in anhydrous DMF (3 mL) was stirred for 30 min at 0° C. under argon, then 23 (0.13 g, 0.45 mmol) in DMF (3 mL) was added. After stirring overnight at room temperature, the reaction mixture was concentrated to dryness, and the crude product was purified by reverse phase HPLC (5-50% ACN in TEAA over 20 min) to give 24 (0.07 g, 50%). Rt (0-10% A in B over 20 min.) 10.36 min.; $^1$H NMR (DMSO-d$_6$) δ: 4.17 (s, 2H, SCH$_2$), 5.31 (s, 2H, CH$_2$), 7.10 (bs, 2H, NH$_2$), 7.29 (m, 3H, H arom.), 7.35 (m, 2H, H arom.), 8.12 (s, 1H, H2); $^{13}$C NMR (DMSO-d$_6$) δ: 34.91 (SCH$_2$), 45.97 (CH$_2$), 119.17 (C5), 127.77, 128.22 and 129.15 (CH), 136.63 (Cq), 147.77 (C8), 152.02 (C4), 152.51 (C2), 154.62 (C6); 169.85 (CO); HRMS (ESI-TOF) m/z calcd for [C$_{14}$H$_{13}$N$_5$O$_2$S+H]316.0868; found 316.0855.

Compound 26

To a mixture of 24 (32 mg, 0.10 mmol) and amino derivative 12 (40 mg, 0.13 mmol) in anhydrous DMF (2 mL) were added PyPOB (52 mg, 0.10 mmol) and DIEA (51 µL, 0.30 mmol). After stirring for 4 h at room temperature, the reaction was complete and the solvent was removed by evaporation. The residue was purified by flash chromatography (0 to 7% MeOH in CH$_2$Cl$_2$) to give compound 25 (60 mg). Isopropylidene groups were then removed by treatment of 25 (30 mg) with trifluoroacetic acid (1 mL, 75% in water). After 3 h at 0° C., the reaction was complete, the solvents were evaporated to dryness. The crude material was taken up in water, the pH was adjusted with a few drops of NH$_4$OH, then lyophilized. Purification by reverse phase HPLC (10-50% ACN in TEAA 15 over 20 min) afforded compound 26 (19 mg, 68%). $^1$H NMR (DMSO-d$_6$) δ: 3.46 (m, 2H, H5' and H5"), 3.99 (m, 1H, H4'), 4.09 (m, 3H, CH$_2$ and H3'), 4.64 (m, 1H, H2'), 5.35 (s, 2H, CH$_2$), 5.89 (d, 1H, H1'), 7.25 (m, 2H, H arom.), 7.34 (m, 3H, H arom.), 8.33 (s, 1H, H2), 8.40 (bs, 4H, NH$_2$), 8.49 (m, 1H, NH), 8.53 (s, 1H, H8); HRMS (ESI-TOF) m/z calcd for [C$_{24}$H$_{25}$N$_{11}$O$_4$S+H]564.1890; found 564.1891.

(m, 1H, H2'), 5.58 (bs, 1H, OH), 5.80 (m, 1H, OH), 5.97 (d, 1H, H1'), 7.43 (bs, 2H, NH$_2$), 8.26 (s, 1H, H2), 8.36 (s, 1H, H8), 9.62 (t, 1H, NH); $^{13}$C NMR (DMSO-d$_6$) δ: 28.35 (CH$_2$), 72.39 (C2'), 73.71 and 73.63 (C3' and CH), 81.22 (Cq), 85.13 (C4'), 88.47 (C1'), 120.15 (C5), 141.18 (C8), 149.06 (C4), 152.94 (C2), 156.84 (C6), 169.86 (CO); HRMS (ESI-TOF) m/z calcd for [C$_{13}$H$_{14}$N$_6$O$_4$+H]319.1155; found 319.1147.

Compound 28

To a degassed solution of 27 (35 mg, 0.11 mmol), 8-bromoadenosine (35 mg, 0.10 mmol) and Et$_3$N (31 μL, 0.22 mmol) in anhydrous DMF (1 mL) were added CuI (2 mg, 10%) and Pd(PPh$_3$)$_2$Cl$_2$ (4 mg, 5%). After stirring for 2 h at 60° C., the solvent was removed by evaporation. The residue was purified by flash chromatography, followed by HPLC (0 to 50% A in B over 20 min.) to give compound 28 (13 mg, 23%). Rt (0-50% A in B over 20 min.) 10.7 min.; $^1$H NMR (DMSO-d$_6$) δ: 3.67 (m, 1H, H5'), 3.68 (m, 1H, H5"), 3.99 (m, 1H, H4'), 4.21 (m, 2H, 2H3'), 4.44 (m, 3H, H4' and CH$_2$), 4.61 (m, 1H, H2'), 4.99 (m, 1H, H2'), 5.17 (d, 1H, OH 3'), 5.37 (d, 1H, OH 2'), 5.50 (t, 1H, OH 5'), 5.57 (d, 1H, OH 2'), 5.80 (d, 1H, OH 3'), 5.94 (d, 1H, H1'), 6.00 (d, 1H, H1'), 7.42 (bs, 2H, NH$_2$), 7.58 (bs, 2H, NH$_2$), 8.15 (s, 1H, H2), 8.29 (s, 1H, H2), 8.38 (s, 1H, H8), 9.81 (t, 1H, NH); $^{13}$C NMR (DMSO-d$_6$) δ: 29.10 (CH$_2$), 62.66 (CH$_2$), 71.42 (C3'), 71.47 (Cq), 72.09 and 72.54 (C2'), 73.62 (C3'), 85.04 and 87.10 (C4'), 88.39 and 89.83 (C1'), 93.51 (Cq), 119.75 and 120.15 (C5), 133.72 (C8), 141.06 (CH$_8$), 148.84 and 149.13 (C4), 153.06 and 153.78 (C2), 156.55 and 156.82 (C6), 170.26 (CO); HRMS (ESI-TOF) m/z calcd for [C$_{23}$H$_{25}$N$_{11}$O$_8$+H]584.1966; found 584.1957.

Scheme 6

27

28

Compound 27

To a mixture of 2',3'-O-isopropylidene-adenosine-5'-carboxylic acid (Meyer, Scott C et al. *Journal of the American Chemical Society*, 2007, 129, p13812-13813) (96 mg, 0.30 mmol) and propargylamine (26 μL, 0.39 mmol) in anhydrous DMF (3 mL) were added PyPOB (156 mg, 0.30 mmol) and DIEA (150 μL, 0.90 mmol). After stirring for 3 h at room temperature, the reaction was complete, the solvent was removed by evaporation and the residue was purified by flash chromatography (0 to 7% MeOH in CH$_2$Cl$_2$). Isopropylidene groups were removed by treatment with trifluoroacetic acid (4 mL, 75% in water). After 3 h at 0° C., the reaction was complete, the solvents were evaporated to dryness. Purification by reverse phase HPLC (0-50% ACN in TEAA over 20 min) afforded compound 27 (62 mg, 66% in two steps). Rt (0-15% A in B over 20 min.) 5.9 min.; $^1$H NMR (DMSO-d$_6$) δ: 3.17 (t, 1H, CH), 4.04 (m, 2H, CH$_2$), 4.14 (m, 1H, H3'), 4.37 (s, 1H, H4'), 4.57

Scheme 7.

a) NBS, DMF, 2 days; b) PPh₃, pyridine, 2 h; NH₄OH, 12 h; c) thioglycolic acid, NaH, DMF, 18 h; d) 9a or 7a, PyBOP, DIEA, DMF, 2-3 h; e) 80% aq. TFA, 2 h.

5'-Azido-5'-deoxy-2',3'-O-isopropylidene-adenosine (6a)

To a solution of 2',3'-O-isopropylidene-adenosine (10.0 g, 32.5 mmol) in pyridine (100 mL) was added dropwise a solution of p-toluenesulfonyl chloride (7.44 g, 7.8 mmol) in pyridine (15 mL) at −20° C. After 48 h in the dark, water (10 mL) was added to the reaction mixture at −20° C. After 15 min, additional water (500 mL) was added at room temperature and the reaction mixture was extracted with ethyl acetate (2×200 mL). The organic layers were dried and evaporated to dryness (13.53 g of crude compound). A mixture of crude 5'-O-tosylated adenosine (5.15 g) and sodium azide (2.90 g, 44.6 mmol) in anhydrous DMF (110 mL) was heated at 80° C. under argon. After 2 h, the reaction was complete and the solvent was removed. The residue was taken up in ethyl acetate and washed with water (twice). The organic layer was dried, evaporated and the crude material was purified by flash chromatography (eluted with 0 to 4% MeOH in CH₂Cl₂) to give 6a (1.50 g, 41% in two steps). The NMR spectra are in accordance with published data (Comstock, L. R., Rajski, S. R. *Tetrahedron* 58, 6019-6026 (2002)).

5'-Azido-8-bromo-5'-deoxy-2',3'-O-isopropylidene-adenosine (8a)

To a stirred solution of 6a (1.00 g, 3.0 mmol) in DMF (mL) was added NHS (1.60 g, 9.0 mmol) at room temperature. After stirring overnight, a second portion of NHS (0.53 g, 3.0 mmol) was added. After stirring for another 18 h at room temperature, the solvent was evaporated, the oily residue was taken up in CH₂Cl₂. The organic layer washed with water (x3), dried over Na₂SO₄, then evaporated to dryness. The crude product was purified by flash chromatography (eluted with 1 to 3% MeOH in CH₂Cl₂) to give 8a (0.50 g, 41%).

5'-Amino-8-bromo-5'-deoxy-2',3'-O-isopropylidene-adenosine (9a)

Reaction of 8a (0.26 g, 0.63 mmol) with PPh₃ (0.25 g, 0.94 mmol) in pyridine, followed by 33% aq. NH₄OH treatment (7 mL) afforded 9a (0.20 g, 81%) after purification by flash chromatography (eluted with 5 to 20% MeOH in CH₂Cl₂).

5'-Azido-8-carboxymethylthio-5'-deoxy-2',3'-O-isopropylidene-adenosine (29)

A solution of thioglycolic acid (0.12 mL, 1.8 mmol) and NaH (0.15 g, 3.6 mmol, 60% in oil) in anhydrous DMF (10 mL) was stirred for 10 min at 0° C. under argon, then 5'-azido-8-bromo-5'-deoxy-2',3'-O-isopropylidene-adenosine (8a) (0.48 g, 1.2 mmol) in DMF (2 mL) was added. After stirring overnight at room temperature, the reaction mixture was concentrated to dryness, and the crude product was purified by flash chromatography (eluted with 1 to 20% MeOH in CH₂Cl₂+1% NH₄OH) to give 29 (0.37 g, 75%) as a pale yellow powder. ¹H NMR (MeOD) δ 1.40 (s, 3H, CH₃), 1.60 (s, 3H, CH₃), 3.46 (dd, 1H, H5'), 3.59 (dd, 1H, H5"), 4.06 (s, 2H, CH₂), 4.29 (m, 1H, H4'), 5.10 (dd, 1H, H3'), 5.73 (dd, 1H, H2'), 6.20 (d, 1H, H1', J=2.3 Hz), 8.13 (s, 1H, H2); ¹³C NMR (MeOD) δ24.09 (CH₃), 26.01 (CH₃), 37.13 (SCH₂), 51.70 (C5'), 82.04 (C3'), 83.12 (C2'), 85.78 (C4'), 89.61 (C1'), 114.28 (C5), 150.38 (C8), 150.57 C4), 151.19 (C2), 154.25 (C6), 173.17 (CO).

5'-Azido-5'-deoxyadenosin-8-yl-thio-N-[(5'-amino-8-bromo-5'-deoxyadenosine)methyl]acetamide (32)

To a mixture of 5'-amino-8-bromo-5'-deoxy-2',3'-O-isopropylidene-adenosine (9a) (58 mg, 0.15 mmol) and 5'-azido-8-carboxymethylthio-5'-deoxy-2',3'-O-isopropylidene-adenosine (29) (70 mg, 0.16 mmol) in anhydrous DMF (2 mL) were added PyPOB (86 mg, 0.16 mmol) and DIEA (58 μL, 0.45 mmol). After stirring at room temperature for 2 h, the reaction was complete and the solvent was removed by evaporation. The residue was purified by flash chromatography (0 to 5% MeOH in CH₂Cl₂) to give O-protected 30. Isopropylidene groups were then removed by treatment with trifluoroacetic acid (2 mL, 75% in water). After 2 h at 0° C., the reaction was complete, the solvents were evaporated to dryness. The crude material was taken up in water, the pH was adjusted with a few drops of NH₄OH, then lyophilized. Purification by reverse phase HPLC (0-50% ACN in TEAA over 20 min) afforded compound 32 (23 mg, 28% in two steps) as a white foam. Rt (0 to 50% ACN in TEAA in 20 min) 11.5 min; $^1$H NMR (DMSO-$d_6$) δ 3.48 (m, 2H, H5'a and H5"a), 3.53 (dd, 1H, H5'b), 3.69 (dd, 1H, H5"b), 4.02 (m, 2H, H4'), 4.14 (s, 2H, $CH_2$), 4.21 (dd, 1H, H3'a), 4.31 (dd, 1H, H3'a), 5.16 (m, 2H, H2'), 5.80 (d, 1H, H1'a, J=5.3 Hz), 5.85 (d, 1H, H1'b, J=6.1 Hz), 7.10 (bs, 2H, $NH_2$), 7.51 (bs, 2H, $NH_2$), 8.12 (s, 1H, H2), 8.31 (s, 1H, H2), 8.56 (bs, 1H, NH); $^{13}$C NMR (DMSO-$d_6$) δ 36.66 ($SCH_2$), 46.12 (C5'a), 51.92 (C5'b), 71.28, 71.36, 71.56 (C2' C3'), 83.69 (C4'a), 84.20 (C4'b), 89.64 (C1'a), 90.05 (C1'b), 119.70 and 120.13 (C5), 127.69 ($CH_8$), 148.91, 150.65 and 151.46 (C8, C4), 152.24 and 153.38 (C2), 154.69 and 155.52 (C6), 167.27 (CO); HRMS (ESI-TOF) m/z calcd for $[C_{22}H_{25}N_{14}O_7SBr+H]$709.1013 and 709.0995; found 709.1018 and 709.1016.

5'-Azido-5'-deoxyadenosin-8-yl-thio-N-[(5'-amino-5'-deoxyadenosine)methyl]acetamide (33)

To a mixture of 29 (43 mg, 0.10 mmol) and 5'-amino-8-bromo-5'-deoxy-2',3'-O-isopropylidene-adenosine (17)$^4$ (44 mg, 1.3 eq.) in anhydrous DMF (2 mL) were added PyPOB (57 mg, 1 eq.) and DIEA (56 µL, 3 eq.). After stirring 2 h at room temperature, the reaction was complete and the solvent was removed by evaporation. The residue was purified by flash chromatography (10 to 20% MeOH in $CH_2Cl_2$) to give O-protected 22 (65 mg). After removal of isopropylidene group as for 30, the crude material was purified by reverse phase HPLC (0-80% ACN in TEAA over 20 min) gave pure 33 (29 mg, 46%). Rt (0 to 50% ACN in TEAA in 20 min) 8.5 min; $^1$H NMR (DMSO-$d_6$) δ 3.46 (m, 2H, H5'a and H5"a), 3.53 (m, 1H, H5'b), 3.69 (m, 1H, H5"b), 4.02 (m, 2H, H4'), 4.13 (m, 3H, H3'b and $CH_2$), 4.31 (dd, 2H, H3'a), 4.72 (t, 1H, H2'b), 5.15 (t, 1H, H2'a), 5.80 (d, 1H, H1'a, J=5.4 Hz), 5.88 (d, 1H, H1'b, J=6.0 Hz), 7.10 (bs, 2H, $NH_2$), 7.30 (bs, 2H, $NH_2$), 8.11 (s, 1H, H2), 8.29 (s, 1H, H2), 8.34 (s, 1H, H8), 8.63 (bs, 1H, NH); $^{13}$C NMR (DMSO-$d_6$) δ 36.62 ($SCH_2$), 41.99 (C5'a), 51.93 (C5'b), 71.29, 71.36, 71.71 (C2' and C3'), 73.10 (C2'), 83.69 (C4'a), 83.76 (C4'b), 88.59 (C1'a), 89.64 (C1'b), 119.70 and 120.01 (C5), 140.90 ($CH_8$), 148.92, 149.64 and 151.45 (C8, C4), 152.24 and 153.16 (C2), 154.72 and 156.63 (C6), 167.38 (CO); HRMS (ESI-TOF) m/z calcd for $[C_{22}H_{26}N_{14}O_7S+H]$631.1908; found 631.1929.

5'-Amino-5'-deoxyadenosin-8-yl-thio-N-[(5'-amino-8-bromo-5'-deoxyadenosine)methyl]acetamide (34)

To a solution of 32 (60 mg, 0.08 mmol) in pyridine (2 mL) was added triphenylphosphine (33 mg, 0.13 mmol). After stirring for 2 h at room temperature, the reaction was complete, then 33% aq. ammonia (2 mL) was added. After stirring overnight, the reaction mixture was evaporated to dryness, and the crude material was triturated in $CH_2Cl_2$. The residue was purified by reverse phase HPLC (5-15% ACN in TEAA over 20 min) to give 34 (22 mg, 40%). Rt (5 to 15% ACN in TEAA in 20 min) 9.7 min; $^1$H NMR (DMSO-$d_6$) δ 2.95 (m, 2H, H5'a and H5"a), 3.47 (m, 2H, H5"b H5'b), 3.97 (m, 2H, H4'a), 4.02 (m, 2H, H4'b), 4.12 (m, 2H, $CH_2$), 4.20 (m, 1H, H3'b), 4.24 (m, 1H, H3'a), 5.00 (t, 1H, H2'a), 5.15 (t, 1H, H2'b), 5.78 (d, 1H, H1'a, J=6.1 Hz), 5.85 (d, 1H, H1'b, J=6.1 Hz), 7.13 (bs, 2H, $NH_2$), 7.51 (bs, 2H, $NH_2$), 8.09 (s, 1H, H2), 8.29 (s, 1H, H2), 8.58 (bs, 1H, NH); $^{13}$C NMR (DMSO-$d_6$) δ 36.66 ($SCH_2$), 41.67 (C5'a), 46.02 (C5'b), 71.29, 71.36, 71.55 and 71.62 (C2' and C3'), 84.22 (C4'), 89.26 (C1'b), 90.88 (C1'a), 119.73 and 120.13 (C5), 127.68 (C8), 148.70, 150.63 and 151.48 (C8, C4), 152.17 and 153.34 (C2), 154.76 and 155.51 (C6), 167.33 (CO); HRMS (ESI-TOF) m/z calcd for $[C_{22}H_{27}N_{12}O_7SBr+H]$683.1108 and 685.1090; found 683.1118 and 685.1093.

II. Biochemical Evaluation

A. Material and Method

Expression, purification and activity assay. His-tagged LmNADK1 wild-type and His-tagged SaNADK were expressed and purified on cobalt-based IMAC resins (Clontech) as previously published[13]. The NAD kinase activity was determined by measuring the absorbance at 340 nm to follow the formation of reduced NADP produced by a coupling enzyme (Glucose-6-phosphate dehydrogenase from yeast). Coupling enzyme and its substrate were purchased from Sigma-Aldrich. The assay was performed in a 0.5 mL sample of (50 mM Tris-HCl pH 7.4, 10 mM $MgCl_2$, 1 mM Glucose-6-phosphate, 2 mM sodium citrate) containing Glucose-6-phosphate dehydrogenase and NADK at 30° C. using a spectrophotometer Eppendorf ECOM 6122.

Inhibitory Potency of NADK Ligands.

For inhibitor assays, IC50 was determined, in the presence of 1 mM NAD and 4 mM ATP (for LmNADK1) or 2 mM ATP (for SaNADK). Dixon plots were used to determine KI in the presence of 4 mM ATP (for LmNADK11) or 2 mM ATP (for Sa NADK) and three NAD concentrations (0.2, 0.5 and 1 mM). It was also checked that the inhibitors had no effect on the coupling enzyme activity.

Bactericidal Activity Assay.

The *Staphylococcus aureus* S25 strain, a human clinical isolate, was grown overnight in brain heart infusion (BHI) broth at 200 rpm and 37° C. Overnight cultures were diluted to $OD_{600nm}$=0.05 in BHI-phosphate buffer saline (25% v/v). Bacteria were grown at 200 rpm and 37° C. until cultures reached $OD_{600nm}$=0.5. Bacterial suspensions were adjusted to a concentration of $2.10^5$ bacteriamL. In a microtiter plate, $2.10^3$ bacteria were incubated overnight at 200 rpm and 37° C. with increasing concentrations of NADK inhibitor in 0.1 mL BHI-phosphate buffer saline (25% v/v) per well. To quantify the bactericidal activity, each bacterial suspension was serially diluted in BHI and plated on BHI agar plates in duplicates. Plates were incubated at 37° C. for 24 h to 48 h and the number of colony forming units was determined.

Human Cell Cytotoxycity.

The human cervical carcinoma HeLa cells were maintained in a humidified atmosphere at 37° C. in 5% $CO_2$ in 75-cm$^2$ plastic flasks in Dulbecco's Modified Eagle Medium (DMEM, Gibco) supplemented with 10% foetal bovine serum (FBS, APP), 100 U/mL penicillin, and 10 µg/mL streptomycin. To evaluate the cytotoxicity of the chemical compounds, HeLa cells were seeded in 96-well plates at low density in presence of DMEM supplemented with 10% FBS and treated with different compounds at 10 µM for 96 h. The final concentration of DMSO in the culture medium was at 0.1% (v/v) to avoid toxicity of the solvent. Cell shape and adherence were monitored and all assays were performed in duplicate. DMSO was used as negative control.

B. Results

Inhibition of LmNADK1

Adenosine derivatives 1-10 were tested on the purified enzyme as previously described [1,1]. Only compound 9 exhibited very weak inhibition ($IC_{50}$ value of 0.3 mM).

In contrast, inhibitions in the micromolar range were detected with the bi-ligands 17, 19 and 22 (see table i). These compounds appear thus as the best inhibitors

TABLE 1

Ki of inhibitors 22, 17 and 19 of NADK from *Lysteria monocytogenes* (Lm) and *Staphylococcus aureus* (Sa)

|  | Inhibitor 22 | Inhibitor 17 | Inhibitor 19 |
|---|---|---|---|
| NADK from Lm | 20 μM | 30 μM | 10 μM |
| NADK from Sa | 15 μM | 50 μM | 5 μM |

Antibacterial Activity of NADK Inhibitor Against *S. Aureus*.

NADK inhibitors 17, 19 and 22 were assayed for bactericidal activity against a human pathogenic strain of *S. aureus*.

Figure 1:
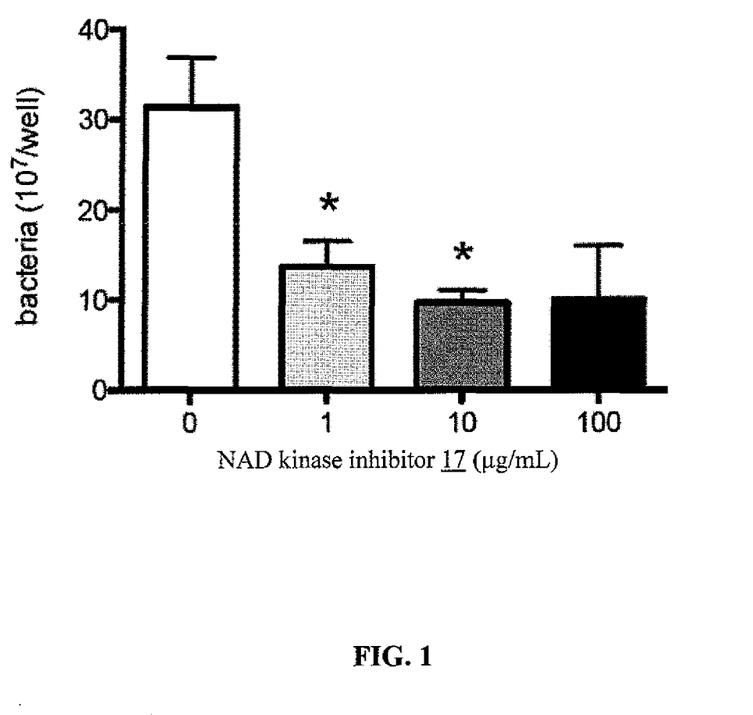
FIGS. 1 to 3. Antibacterial effect of NADK inhibitors 17, 19 and 22 on *S. aureus*.
Figure 2:
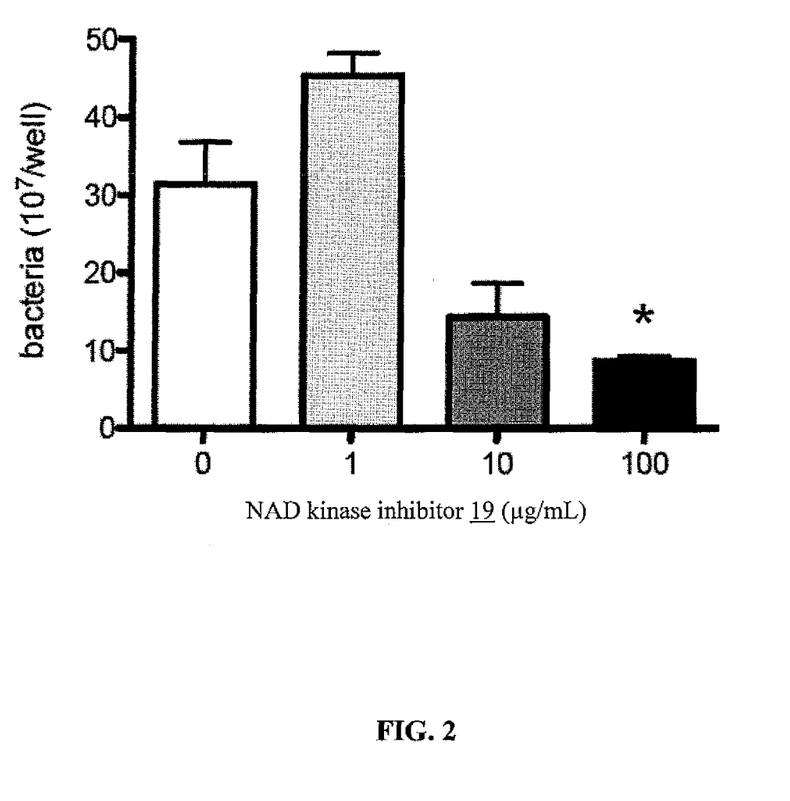
Figure 3:
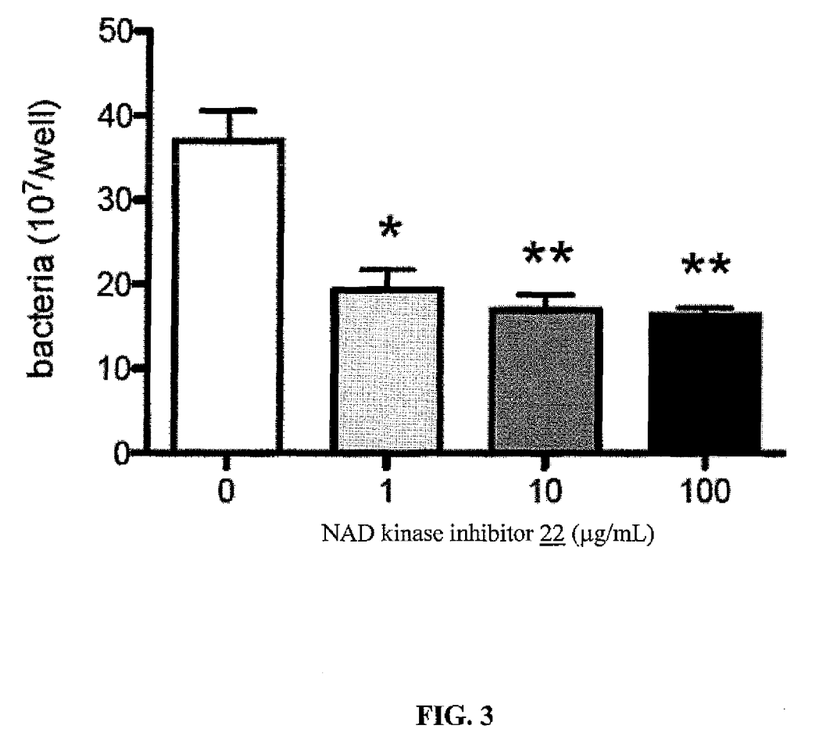

It can be seen from FIGS. 1 to 3 that these NADK inhibitors, present a significant bactericidal activity at 1 μg/mL for inhibitors 17 and 22, and at 10 μg/mL for inhibitor 19. Besides, further increasing the concentration of the inhibitors do not lead to any increase in bactericidal activity. These efficiencies compare favorably with that of reference compounds such as vancomycin (8 μg/mL).

Cytotoxicity

In parallel, cytotoxicity was assayed on Hela cells in culture for 96 hrs. No change in cell shape and multiplication rate was observed when tested at 10 micromolar.

References

1. Pucci, M. J. (2006) *Biochem. Pharmacol.* 71, 1066-1072
2. Gerdes, S. Y., Scholle, M. D., D'Souza, M., Bernal, A., Baev, M. V., Farrell, M., Kurnasov, O. V., Daugherty, M. D., Mseeh, F., Polanuyer, B. M., Campbelli, J. W., Anantha, S., Shatalin, K. Y., Chowdhury, S. A., Fonstein, M. Y., and Osterman, A. L. (2002) *J. Bacteriol.* 184, 4555-4572
3. Kobayashi, K., Ehrlich, S. D., Albertini, A., Amati, G., Andersen, K. K., Arnaud, M., Asai, K., Ashikaga, S., Aymerich, S., Bessieres, P., Boland, F., et al. (2003) *Proc. Natl. Acad. Sci. U.S.A.* 100, 4678-4683
4. Suzuki, N., Okai, N., Nonaka, H., Tsuge, Y., Inui, M., and Yukawa, H. (2006) *Appl. Environ. Microbiol.* 72, 3750-3755
5. Sassetti, C. M., Boyd, D. H., and Rubin, E. J. (2003) *Mol. Microbiol.* 48, 77-84
6. Thanassi, J. A., Hartman-Neumann, S. L., Dougherty, T. J., Dougherty, B. A., and Pucci, M. J. (2002) *Nucleic Acids Res.* 30, 3152-3162
7. Zalacain, M., Biswas, S., Ingraham, K. A., Ambrad, J., Bryant, A., Chalker, A. F., Iordanescu, S., Fan, J., Fan, F., and Lunsford, R. D. (2003) *J. Mol. Microbiol. Biotechnol.* 6, 109-126
8. Grose, J. H., Joss, L., Velick, S. F., and Roth, J. R. (2006) *Proc. Natl. Acad. Sci. U.S.A.* 103, 7601-7606
9. Kawai, S., Mori, S., Mukai, T., Suzuki, S., Yamada, T., Hashimoto, W., and Murata, K. (2000) *Biochem. Biophys. Res. Commun.* 276, 57-63
10. Lerner, F., Niere, M., Ludwig, A., and Ziegler, M. (2001) *Biochem. Biophys. Res. Commun.* 288, 69-74
11. Poncet-Montange, G., Assairi, L., Arold, S., Pochet, S., Labesse, G., (2007), *J. Biol. Chem*, Vol. 282, No. 47, pp. 33925-33934.
12. Kikugawa, K. and Ichino, M. Direct halogenation of sugar moiety of nucleosides. *Tet. Lett.* 12, 87-90 (1971).
13. Schaffrath, C., S. Cobb, L., et al. Cell-Free Biosynthesis of Fluoroacetate and 4-Fluorothreonine in *Streptomyces Cattleya* 13. *Angew. Chem. Int. Ed.* 41, 3913-3915 (2002).
14. Jawalekar, A. M., N. Meeuwenoord, et al. Conjugation of Nucleosides and Oligonucleotides by [3+2]Cycloaddition. *J. Org. Chem.*, 73, 287-290 (2008).
15. Kolb, M., C. Danzin, et al. Synthesis and biochemical properties of chemically stable product analogs of the reaction catalyzed by S-adenosyl-L-methionine decarboxylase. *J. Med. Chem.* 25, 550-556 (1982).

The invention claimed is:

1. A compound of formula (A):

(A)

or a tautomer, stereoisomer, mixture of stereoisomers, or pharmaceutically acceptable salt thereof, wherein $R_1$ is H, $C_1$-$C_6$ alkyl, $C_2$-$C_6$ alkenyl, or $C_2$-$C_6$ alkynyl;

an alkyl, alkenyl, or alkynyl group in $R_1$ if present is optionally substituted by $SR_5$, $NR_5R_{5A}$, or $OR_5$;

$R_2$ is H, F, Cl, Br, I, $OR_6$, or $NHR_7$;

$R_3$ is H, Cl, Br, F, I, $OR_8$, or $NHR_9$;

$R_4$ is H, Cl, Br, F, I, $CH_3$, $SCH_2COOH$, $SR_{10}$, $SeR_{11}$, $CH_2R_{12}$, $C\equiv CR_{13}$, $CH=CHR_{14}$, or $S(CH_2)_nC(=O)R_{17}$;

$X_1$ is —S—, —Se—, —$CH_2$—, —CH=CH—, or —C≡C—;

$X_2$ is a single bond, $C_1$-C4 alkylene, $C_2$-$C_4$ alkenylene, or $C_2$-$C_4$ alkynylene;

$X_3$ is —NHC(=O)—, —C(=O)NH—, —$NR_{15}$—, —$SO_2NH$—, —$NHSO_2$—, —$CH_2$—, —O—, or —S—;

Z is of formula or Z is $C_6$-$C_{10}$ aryl, or 5 to 7 membered heteroaryl, arylalkyl, or heteroarylalkyl, an aryl or heteroaryl group in Z is optionally substituted with from 1 to 3 $R_0$ groups;

$R_0$ is F, Cl, Br, I, OH, $NH_2$, $NO_2$, $C_1$-$C_6$ alkyl, $C_2$-$C_6$ alkenyl, or $C_2$-$C_6$ alkynyl;

$R_5$, $R_{5A}$, $R_6$, $R_7$, $R_8$, $R_9$, and $R_{15}$ are each independently H, $C_1$-$C_6$ alkyl, $C_2$-$C_6$ alkenyl, or $C_2$-$C_6$ alkynyl;

$R_{10}$, $R_{11}$, $R_{12}$, $R_{13}$, and $R_{14}$ are each independently $C_1$-$C_6$ alkyl, $C_2$-$C_6$ alkenyl, or $C_2$-$C_6$ alkynyl;

$R_{16}$ is OH, $NH_2$, $N_3$, or $OCH_2CH=CH$;

$R_{17}$ is OH or $NH(CH_2)_p$Ar;

Ar if present in $R_{17}$ is an aryl group optionally substituted by Br, C≡CH;

m is 0 or 1;

n is 1, 2, or 3; and p is 1, 2, or 3.

2. The compound of claim 1, which is of formula (Ia):

(Ia)

3. The compound of claim 2, wherein $X_3$ is —O— or —NH—.

4. The compound of claim 1, which is of formula (Ib):

(Ib)

5. The compound of claim 1, wherein $X_2$ is —$CH_2$—.

6. The compound of claim 1, wherein $R_{16}$ is $NH_2$ or OH.

7. The compound of claim 1, wherein $R_2$ is H.

8. The compound of claim 1, wherein $R_1$ is H.

9. The compound of any claim 1, wherein $R_3$ is H.

10. The compound of claim 1, wherein $R_4$ is H.

11. The compound of claim 1 wherein the compound is 5'-amino-5'-deoxyadenosin-8-yl-thio-N-[(5'-amino-5'-deoxyadenosine)methyl]acetamide; 8-[3-N-(5'-deoxyadenosyl)aminoprop-1-ynyl]adenosine; 8-[3-(5'-deoxyadenosyl)methoxyprop-1-ynyl]adenosine, or any combination thereof.

12. A pharmaceutical composition comprising the compound of claim 1, in admixture with one or more pharmaceutically acceptable excipients.

13. The compound of claim 1, wherein the compound is suitable for prevention, treatment, or both prevention and treatment of a bacterial infection.

14. A method for preparing the compound of claim 2, the method comprising:
coupling a compound of formula (IIa) with a compound of formula (IIIa),

(IIa)

(IIIa)

thereby obtaining a compound comprising hydroxyl groups,
deprotecting hydroxyl groups of the compound comprising hydroxyl groups, and
optionally recovering a compound of formula (Ia),
wherein Hal is Br, I, or Cl, and
with the proviso that any hydroxyl groups present in Z are protected by a hydroxyl protecting group.

15. A method for preparing the compound of claim 4, the method comprising:
coupling a compound of formula (IIb) with a compound of formula (IIIb), (IIb)

(IIIb)

thereby obtaining a compound comprising hydroxyl groups;
deprotecting hydroxyl groups of the compound comprising hydroxyl groups; and
optionally recovering a compound of formula (Ib),
wherein $R_{17}$ is $OR_{18}$ or Hal, and
$R_{18}$ is H or $C_1$-$C_6$ alkyl, or C(=O)$OR_8$ is an activated ester, with the proviso that any hydroxyl groups present in Z are protected by an hydroxyl protecting group.

16. A chemical probe comprising the compound of claim 1, coupled to a detectable label.

17. A method for screening a molecule inhibiting NAD kinase, the method comprising:
contacting NAD kinase with the chemical probe of claim 16 with a molecule to be screened;
determining a quantity of chemical probe bound or unbounded to the NAD kinase; and deducing from the quantity if the molecule is an inhibitor of the NAD kinase.

18. A method of treating a bacterial infection, the method comprising administering the compound of claim 1 to a subject in need thereof.

* * * * *